United States Patent
Minatelli et al.

(10) Patent No.: US 9,592,264 B2
(45) Date of Patent: Mar. 14, 2017

(54) DELIVERY SYSTEM FOR SAW PALMETTO EXTRACT AND CAROTENOID

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 197 days.

(21) Appl. No.: 14/226,869

(22) Filed: Mar. 27, 2014

(65) Prior Publication Data

US 2014/0302136 A1 Oct. 9, 2014

Related U.S. Application Data

(60) Provisional application No. 61/808,754, filed on Apr. 5, 2013.

(51) Int. Cl.
| | |
|---|---|
| *A61K 31/01* | (2006.01) |
| *A61K 36/81* | (2006.01) |
| *A61K 36/889* | (2006.01) |
| *A61K 9/50* | (2006.01) |
| *A61K 9/48* | (2006.01) |

(52) U.S. Cl.
CPC .......... *A61K 36/81* (2013.01); *A61K 9/4808* (2013.01); *A61K 9/5084* (2013.01); *A61K 31/01* (2013.01); *A61K 36/889* (2013.01)

(58) Field of Classification Search
None
See application file for complete search history.

(56) References Cited

U.S. PATENT DOCUMENTS

| | | | |
|---|---|---|---|
| 6,261,607 B1* | 7/2001 | Newmark | A61K 36/185 424/702 |
| 6,319,524 B1 | 11/2001 | Gregg, Jr. | |
| 6,669,968 B2 | 12/2003 | Gregg, Jr. | |
| 7,238,373 B2 | 7/2007 | Meyrowitz | |
| 8,221,803 B1* | 7/2012 | Pinski | A61K 31/01 424/727 |
| 8,354,126 B1 | 1/2013 | Pinski | |
| 2002/0001633 A1 | 1/2002 | Revel | |
| 2005/0008690 A1 | 1/2005 | Miller | |
| 2005/0191369 A1 | 9/2005 | Harvey | |
| 2006/0068038 A1 | 3/2006 | Harvey et al. | |
| 2006/0069151 A1 | 3/2006 | Barella et al. | |
| 2007/0243210 A1 | 10/2007 | Keefe et al. | |

FOREIGN PATENT DOCUMENTS

WO 2006035416 4/2006

OTHER PUBLICATIONS

Sathish et al., "HPLC Method for the Determination of Lycopene in Crude Oleoresin Extracts," Asian Journal of Chemistry, vol. 21, No. 1 (2009), pp. 139-148.
The United States Pharmacopeial Convention, "Saw Palmetto," Revision Bulletin, Jun. 1, 2013, pp. 1-3.

* cited by examiner

*Primary Examiner* — Terry A McKelvey
*Assistant Examiner* — Catheryne Chen
(74) *Attorney, Agent, or Firm* — Allen, Dyer, Doppelt, Milbrath & Gilchrist, P.A.

(57) ABSTRACT

A medicine delivery system delivers medicine such as a dietary supplement to improve prostate health and includes an outer capsule containing a saw palmetto extract and an inner capsule within the outer capsule and containing a carotenoid. The outer capsule is formed to dissolve in the stomach when ingested to release the saw palmetto extract into the stomach and the inner capsule is formed to pass into the duodenum to dissolve and release the carotenoid into the duodenum.

13 Claims, 1 Drawing Sheet

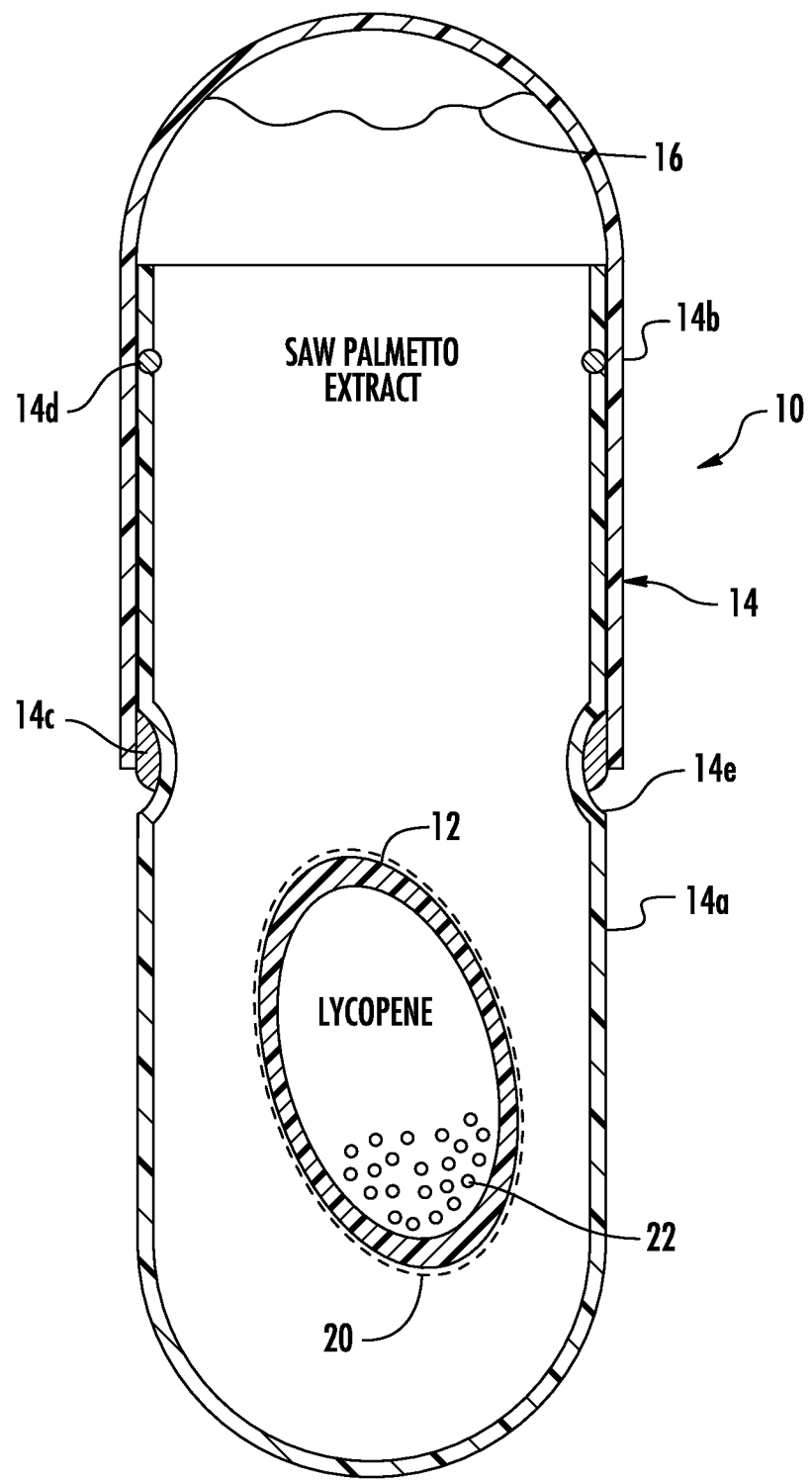

DELIVERY SYSTEM FOR SAW PALMETTO EXTRACT AND CAROTENOID

PRIORITY APPLICATION(S)

This application is based upon provisional application Ser. No. 61/808,754 filed Apr. 5, 2013, the disclosure of which is hereby incorporated by reference in its entirety.

FIELD OF THE INVENTION

This invention relates to the field of dietary supplements, and more particularly, a medicine delivery system for delivering a dietary supplement as a medicine to a human to improve prostate health, such as saw palmetto extract, and a carotenoid, such as lycopene.

BACKGROUND OF THE INVENTION

Saw Palmetto (*Serenoa repens*) is a shrubby palm that grows only in the southeastern United States, and is most prolific on pine flatwoods in peninsular Florida and southern Georgia. The saw palmetto grows a seed stalk (spadix) in late spring, which flowers and then develops a hard green fruit about the size of a small olive. The fruit ripens in the summer, turning shades of yellow, orange and black. The ripe fruit is then harvested by hand during the late summer and early fall. Typical yields in harvestable areas range from a low of 200 pounds to more than 1,000 pounds of berries per acre.

Saw palmetto berries have been ingested by Native Americans for many centuries. Early in the 20th century, naturopathic physicians in the U.S. began prescribing a tea made from saw palmetto berries as a mild diuretic and for genitourinary problems. It became a popular male tonic, but eventually the therapeutic value of the tea (a water extract) came into question and in the early 1940's it lost both its popularity and its inclusion in the National Formulary. Research in Europe in the 1960's led to the identification of the lipid portion of the berry and its medically active components, including free fatty acids and sterols, also referred to in the art as phytosterols, since they originate in plant tissue.

In recent years, saw palmetto extracts have been increasingly used by consumers to treat prostate disorders. Saw palmetto extracts may be produced by a variety of processes that remove oil from the saw palmetto berry, leaving the inert berry mass that is discarded. Most saw palmetto extracts are made using supercritical $CO_2$ extraction. The saw palmetto berries are broken down into free fatty acids, phytosterols (plant sterols), free fatty acids and monoglycerides to form the saw palmetto extract. The United States Pharmacopeia (USP) has developed some minimum standards for saw palmetto extract as a nutraceutical supplement based on the total fatty acids, fatty acid profile, total fatty alcohols, and phytosterol levels. These standards are set forth in the U.S. Pharmacopeia Saw Palmetto Extract, USP 26-NF21, First Supplement 2003, pages 3024-25, the disclosure which is hereby incorporated by reference in its entirety.

The saw palmetto, fat soluble extract from saw palmetto berries is believed to inhibit the conversion of testosterone (DHT), which is thought to be responsible for enlarging the prostate. Also, the saw palmetto extract may inhibit the binding of DHT to receptors, thus blocking DHT's action and promoting the breakdown of that compound.

U.S. Nutraceuticals manufactures and sells saw palmetto extracts such as described in commonly assigned U.S. Pat. Nos. 6,319,524 and 6,669,968, the disclosures which are hereby incorporated by reference in their entirety. It has been determined that the free fatty acid content that is particular to saw palmetto extracts, such as the $CO_2$ extracts, are not triacylglycerides similar to many seed oils. Instead, they are acidic free fatty acids and somewhat unusual as seed oil extracts that are usually neutral triacylglycerides. These acidic free fatty acids are not compatible with lycopene, which is often used to treat prostate deficiencies and aid in preventing prostate cancer. It is desirable to be able to present both the saw palmetto extract and the lycopene together in one oral dosage form without degrading the lycopene that would result when the lycopene is mixed with the higher acidic levels of the saw palmetto extract. Both lycopene and saw palmetto extract have been clinically evaluated and shown to be effective in maintaining prostate health. Saw palmetto extract has been shown to mitigate the symptoms of benign prostatic hyperplasia (BPH), while lycopene has been shown to be effective in possibly preventing prostate cancer.

SUMMARY OF THE INVENTION

A medicine delivery system delivers a capsulated dietary supplement composition as a medicine to humans to improve prostate health and includes an outer capsule containing a saw palmetto extract and an inner capsule within the outer capsule and containing a carotenoid. The outer capsule is formed to dissolve in the stomach when ingested to release the saw palmetto extract into the stomach. The inner capsule is formed to pass into the duodenum to dissolve and release the carotenoid into the duodenum.

In an example, the carotenoid is formed as a carotene and in an example as lycopene formed from a natural tomato extract and in one example as lycopene beadlets. In an example, the saw palmetto extract includes at least 90% total saw palmetto lipids. The lipids are formed as fatty acids, sterols and fatty alcohols in an example. The saw palmetto extract may be made by a process of extracting the saw palmetto lipids by contacting ground saw palmetto berries with a substantially continuous flow of carbon dioxide under pressure in a supercritical $CO_2$ extraction process.

In another example, the inner capsule is formed with an acid resistant coating to prevent the inner capsule from dissolving within the stomach after it is released from the dissolved outer capsule and allow the inner capsule to pass into the duodenum and dissolve within the duodenum. The carotenoid may be formed as an acid resistant time-released carotenoid such as a lycopene beadlet formed to release the carotenoid or lycopene over a period of time within the duodenum.

A method is also disclosed that includes administering to a human a therapeutically effective amount of saw palmetto extract into the stomach of a human followed by administering to the human a therapeutically effective amount of a carotenoid within the duodenum. An example is providing the outer capsule and inner capsule with the respective saw palmetto extract and carotenoid such as lycopene.

BRIEF DESCRIPTION OF THE DRAWINGS

Other objects, features and advantages of the present invention will become apparent from the detailed description of the invention which follows, when considered in light of the accompanying drawings in which:

FIG. 1 is an example of a medicine delivery system that delivers a capsulated dietary supplement composition as a medicine to humans and includes an inner capsule containing lycopene and an outer capsule containing saw palmetto extract, in accordance with a non-limiting example.

DETAILED DESCRIPTION OF THE PREFERRED EMBODIMENTS

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

FIG. 1 shows a medicine delivery system illustrated generally at 10 that includes an inner capsule 12 containing a carotenoid such as lycopene and contained within an outer capsule 14 containing a saw palmetto extract 16. The outer capsule 14 dissolves in stomach acids after ingestion, releasing the saw palmetto extract into the stomach to be absorbed, while the inner capsule 12 survives the acidic environment of the stomach and passes into the duodenum where the carotenoid contents, such as the carotene, e.g., lycopene, is released in the now less acidic environment of the duodenum. This can be accomplished in one non-limiting example by adding an acid resistant coating shown by the dashed lines at 20 onto the inner capsule 12 after the inner capsule is manufactured and prior to assembly of the inner capsule 12 into the outer capsule 14 and forming the final capsule product. This function can also be accomplished by adding an acid resistant form of lycopene into the inner capsule, for example, using acid resistant timed released technology to release the lycopene under the less acidic conditions of the duodenum. An acid resistant time-release lycopene beadlet 22 could be contained within the inner capsule 14 and formed to release the carotenoid, i.e., lycopene, over a period of time within the duodenum.

The outer capsule 14 may be formed as a two-piece body with an open ended lower capsule section 14a that extends substantially the entire length of the outer capsule and an upper capsule section 14b that is received over the open end of the lower capsule section 14a. The two capsule sections, 14a, 14b may be heat melted together and fused at seal zones 14c and 14d or fused together in some other manner such as by added adhesive. The lower capsule section 14a may include a central ring 14e that is concave in one example to enhance a seal such as including a fused or melted joint at the seal zone 14c. The inner capsule 12 can be formed in a similar manner. The outer capsule sections can be formed from a material that dissolves in stomach acids or dissolves in a liquid environment such that it begins to dissolve as soon as it enters the stomach of a human.

The pH of the stomach is about 1-3 with chyme corresponding to the semi-fluid mass of partly digested food having a pH of about 2. To raise the pH, the duodenum secretes a hormone, cholecysteokinin (CCK), which causes the gallbladder to contract and release alkaline bile into the duodenum, which also produces the hormone secretions to stimulate the pancreatic secretion of large amounts of sodium bicarbonate. This raises the chyme's pH to about 7 before it reaches the jejunum. It is protected by a thick layer of mucus and uses the neutralizing actions of the sodium bicarbonate and bile. The duodenum is not as sensitive to the highly acidic chyme as a result of the small intestine. At a pH of 7, the enzymes that were present from the stomach are no longer active and this leads to further breakdown of nutrients still present by an anaerobic bacteria. Some studies have indicated that the median gastric pH is about 1.7 and the median duodenal pH is about 6.1.

The saw palmetto extract in an example is formed as a super critical CO2 fluid solvent derived extract from saw palmetto berries. The saw palmetto extract may be formed from the processes and methods described in the above-identified and incorporated by reference '968 and '524 patents.

A lycopene stability study protocol with saw palmetto revealed the instability of lycopene when mixed with saw palmetto extract. A saw palmetto extract of 320 milligrams (mg) was mixed with different levels of lycopene including 5 mg, 10 mg and 15 mg. For example, the materials include a tomato lycopene extract as manufactured as the Parry Tomato Lycopene Complex from Parry Nutraceuticals of E.I.D. Parry (India) Ltd and a saw palmetto extract such as manufactured from Valensa International of Eustis, Fla. A lycopene analytical reference standard was available and HPLC analysis method referenced with the lycopene content and analyzed by HPLC and UV-VIS spectrophotometry after 15 and 30 days intervals. The results are shown below:

Objective:

To study the stability of Lycopene in combination with Saw Palmetto Extract under refrigerated conditions (10° C.)

Product/Formulation Details:
  a) Saw Palmetto Extract 320 mg+5 mg Lycopene
  b) Saw Palmetto Extract 320 mg+10 mg Lycopene
  c) Saw Palmetto Extract 320 mg+15 mg Lycopene Materials:
  a) Tomato Lycopene extract—from M/s Phytoremedies, Batch No: PP/LO-18/001/2009—Lycopene content: 18% w/w
  b) Saw Palmetto Extract—from M/s Valensa International, Lot 091121SPCH-O
     Total Fatty Acid content: 90.1% w/w
  c) Lycopene Analytical reference standard: 95.5% pure From M/s ChromaDex Method:

Reference: *HPLC analysis method—Asian Journal of chemistry, Vol. 21, No. 1* (2009)
  a) Analytical Balance—with accuracy of 0.01 mg
  b) Waters HPLC Gradient system with PDA Detector and column oven
  c) Column: C18, 15.0 cm×4.6 mm; SS; 3μ
  d) HPLC solvents: Acetonitrile, Methanol, Tetra hydro furan Study Parameter:

Lycopene content by HPLC & UV-Vis Spectrophotometry after 15 and 30 days interval A table of results of the stability data of the lycopene content after 30 days are shown below. The drop in lycopene content occurred at 25° C. as indicated. These results show the beneficial aspects of using the capsule within the capsule and its function as described above with reference to FIG. 1 in order to solve the incompatibility of mixing the saw palmetto extract and the lycopene.

STABILITY DATA OF LYCOPENE
CONTENT AFTER 30 DAYS

| Sample | Initial | 25° C. 55-60% RH | % Drop | 40° C. 75% RH | % Drop |
|---|---|---|---|---|---|
| Lycopene | 17.06 | 17.19 | −0.76 | 17.00 | 0.35 |
| SPL 001 | 1.41 | 1.31 | 7.09 | 1.20 | 14.89 |
| SPL 002 | 3.07 | 2.68 | 12.70 | 2.64 | 14.01 |
| SPL 003 | 4.06 | 3.51 | 13.55 | 3.72 | 8.37 |
| Average | | | 11.11 | | 12.42 |
| SPLE 001 | 1.45 | 1.39 | 4.14 | 1.31 | 9.66 |
| SPLE 002 | 2.96 | 2.72 | 8.11 | 2.61 | 11.82 |
| SPLE 003 | 3.98 | 3.73 | 6.28 | 3.70 | 7.04 |
| Average | | | 6.18 | | 9.50 |

SPL 001 320 mg of Saw Palmetto Extract + 5 mg Lycopene
SPL 002 320 mg of Saw Palmetto Extract + 10 mg Lycopene
SPL 003 320 mg of Saw Palmetto Extract + 15 mg Lycopene
SPLE 001 320 mg of Saw Palmetto Extract + 5 mg Lycopene + 4 mg Vit-E
SPLE 002 320 mg of Saw Palmetto Extract + 10 mg Lycopene + 4 mg Vit-E
SPLE 003 320 mg of Saw Palmetto Extract + 15 mg Lycopene + 4 mg Vit-E
No drop in Lycopene content at 10° C., however, further details may be obtained after 60 days of analysis.

As noted before, the inner capsule 12 is formed in one example with an acid resistant coating 20 to prevent the inner capsule from dissolving within the more acidic environment of the stomach and allowing the inner capsule to dissolve within the less acidic environment of the duodenum. This acid resistant coating 20 could be similar to enteric coatings that could include different formulations, including systemic enzyme formulas that contain phthalates in the coating or various dense vegetable cellulose coatings. Other polymer film formulations could be used as a coating. The shell material of the inner capsule 12 could also be formed of a material that withstands the more acidic environment of the stomach. It is also possible to design a beadlet as a timed release carotenoid, such as a lycopene beadlet, that is formed as a layered beadlet that may release any carotenoids over a period of time, such as the lycopene.

The saw palmetto extract can be formed using various techniques. One technique is extracting the saw palmetto berries with a substantially continuous flow of carbon dioxide under pressure. A preferred example for extraction is the DeepExtract™ ultra-high pressure supercritical CO2 technology as developed by Valensa International (U.S. Nutraceuticals) of Eustis, Fla. It is possible to produce a rich total extraction product of native organic saw palmetto berries. This is an all-natural process that does not use chemical solvents. The dark color of the saw palmetto extract indicates a premium product with the highest efficacy available. Independent assays have shown that the extract contains three times the beta carotene, ten times the amount of lutein and 30 times the zeaxanthin of typical saw palmetto extracts. The table below shows typical extract analysis versus the USP specification for one type of extract sold as a Prostate Formula.

| PARAMETER | Extract | USP Specification |
|---|---|---|
| Total Fatty Acids | 90% | 70-95% |
| Total Sterols | 0.35% | 0.20-0.50% |
| Total Fatty Alcohols | 0.18% | 0.15-0.35% |
| Iodine Value | 42 | 40-50 |
| Saponification Value | 230 | 210-250 |
| Unsaponifiable Matter | 2.0% | 1.8-3.5% |
| Residual Solvent | Absent | |
| Heavy Metals | <10 ppm | |

The proprietary DeepExtract™ supercritical CO2 process from Valensa creates the highest quality materials. A O2B™ peroxidation blocker stabilization technology may be added to the saw palmetto extract to ensure long-term product stability and efficacy.

It is also possible to form a Palmetto Rosso™ saw palmetto extract, based on a process that has been fine tuned to produce a visually appealing, brilliant natural rose-colored extract.

Specifications for Saw Palmetto
Ingredient Declaration
*Serenoa repens* (W. Bartram) Fruit Supercritical CO2 Extract

| Physical Properties | |
|---|---|
| Appearance | Oily brown liquid, pourable at room temperature |
| Odor | Characteristic and aromatic |
| Solubility | Insoluble in water. Miscible with oils and non-polar solvents |
| Refractive Index | 1.400-1.500 |
| Relative Density | 0.850-0.950 |
| Moisture | <1.5% (Karl Fischer) |
| Chemical Properties | |
| Total Fatty Acids | 85-95% (GC)* |
| Total Sterols | 0.20-0.50% (GC)* |
| Total Fatty Alcohols | 0.15-0.35% (GC)* |
| Iodine Value | 40-50 USP <401> |
| Saponification Value | 210-250 USP <401> |
| Unsaponifiable Matter | 1.8-3.5% USP <401> |
| Peroxide Value | <5.0 USP <401> |
| Acid Value | <230 USP <401> |
| Residual Solvent | Absent |
| Heavy Metals | <10 ppm AOAC |
| Microbiological | |
| Total Plate Count | <1000 cfu/g USP <61> |
| Yeast and Mold | <100 cfu/g |
| *E. coli* | Negative |
| *Salmonella* | Negative |
| *S. aureus* | Negative |
| *Pseudomonas* | Negative |
| Storage | |
| Conditions | Tightly closed containers in a cool, dry, dark location |
| Shelf-life | 24 months minimum |
| Packaging | 25 or 180 kg food-grade HDPE containers |

It is possible to use the Deep Extract™ ultra high pressure, dioxide extraction technology that yields more micronutrients. Super critical CO2 extraction is advantageous over other techniques such as tinctures using alcohol extraction, steam distillation, expeller pressing, sometimes called "cold pressing," and chemical solvent extraction. When carbon dioxide (CO2) gas is compressed above 73 bar at a temperature above 31° C. it transforms into a dense gas known as supercritical CO2, which has an extremely high solvating capacity with the power to extract the constituents of botanicals. Because its solvating capacity is a function of its density, by changing its density with pressure, it is possible to select the quality, quantity and specific principals of the targeted extract.

As noted before, the inner capsule 12 shown in FIG. 1 contains a carotenoid, such as the preferred lycopene. The carotenoids can be produced from fats and other basic organic metabolic building blocks. Carotenoids belong to the category of tetraterpenoids that contain 40 carbon atoms built from 4 terpene units containing 10 carbon atoms. The carotenoids usually have the form of a polyene hydrocarbon chain that is sometimes terminated by rings and may or may not have additional oxygen atoms attached. The carotenoids with the molecules containing oxygen include lutein and zeaxanthin and are known as xanthophylls, while the unoxygenated as oxygen free carotenoids are known as carotenes and include lycopene as described as the preferred composition of the inner capsule. It is chemically a carotene but has no vitamin A activity. It is an important intermediate in the biosynthesis of many carotenoids, including beta carotene. It is a polyunsaturated hydrocarbon as an unsubstituted alkene. Its eleven conjugated double bonds give lycopenes deep red color and are responsible for its antioxidant activity. In vitro, lycopene quenches singlet oxygen more efficiently that vitamin E. A lycopene metabolite, apo-10' lycopenal may be more important in the metabolism of hepatic lipids.

The saw palmetto composition may be formed as an extract of saw palmetto berries and contain at least 90% total saw palmetto lipids and include fatty acids, sterols, fatty alcohols, and different combinations and without a solvent residue. An oral unit dose contained within the outer capsule may contain at least 160 mg of saw palmetto lipids in one example, and in another example, about 320 mg of saw palmetto lipids. The composition may also include a predetermined blend of saw palmetto sterols, saw palmetto triglycerides and saw palmetto fatty acids, such as greater than 0.2% saw palmetto sterols. In one example, the solvent residue is an organic solvent and selected from ethanol and hexane.

The saw palmetto berries as originally harvested may be extracted by supercritical fluid extraction using CO2 under high pressure, for example, using the deep extract technology from Valensa International. The saw palmetto berries are dried and ground, and the berries extracted with CO2 under high pressure and the extracted compound separated from the CO2. In one example, the extracting occurs in an extractor vessel by contacting the ground saw palmetto berries with CO2 in an extraction pressure of at least 500 bar and at a temperature lower than about 80° C. to extract the saw palmetto compounds into the CO2. The extracted saw palmetto compounds are separated from the CO2 in a separator vessel into at least a first fraction and decreasing the pressure to a predetermined first separation pressure lower than the previous extraction pressure and at a temperature sufficient to prevent the carbon dioxide from solidifying.

In another example, as the high pressure CO2 flows through the product, it behaves as a solvent and extracts those saw palmetto compounds which are soluble in the fluid. In one preferred extraction pressure, 550 bar is used and at a preferred first separation pressure, 250 bar. Extracting can be conducted at a temperature from about 45° to about 80° C. and preferably under a substantially continuous flow of carbon dioxide. Different separation vessels may be used, including a third separation vessel having a third separation pressure lower than a second separation pressure to separate a third fraction of extracted compounds from carbon dioxide. Sequentially, the CO2 may flow into a third separation vessel and through a pressure reducer and temperature regulator and a third fraction is collected. Carbon dioxide may be returned to storage for further use. Different plural separations may be conducted sequentially and in a substantially continuous flow with each subsequent separation including a lower predetermined separation pressure. This is referred to as cascading separations in the industry and allows for separating the extracted saw palmetto compounds from the carbon dioxide into a plurality of fractions.

Tables 1-4 show several examples of the method for extracting the saw palmetto berries. Table 1 shows the results of extraction of saw palmetto berries at a pressure of at least 500 bar, followed by a sequence of three separations at 200 bar, 120 bar and 30 bar, respectively. As shown in Table 1, fraction 1 obtained during the first separation of 200 bar contains twice the concentration of phytosterols found in the extract. Tables 2, 3 and 3 summarize data for an extraction method having two sequential separations.

Further details of the process are set forth in the incorporated by reference '524 and '968 commonly assigned patents.

TABLE 1

SUPERCRITICAL EXTRACTION OF SAW PALMETTO OIL WITH FRACTIONATION INTO A HIGH-STEROL FRACTION

| VESSEL | PRESSURE | TEMP. | FRACTION | YIELD % | % FATTY ACIDS | % STEROLS | % FATTY ALCOHOLS |
|---|---|---|---|---|---|---|---|
| EXTRACTOR | 500 bar | 80° C. | WHOLE EXTRACT | 13.7 | 91.1 | 0.24 | 0.22 |
| SEPARATOR 1 | 200 bar | 65° C. | FRACTION 1 | 1.1 | 81.2 | 0.40 | 0.48 |
| SEPARATOR 2 | 120 bar | 48° C. | FRACTION 2 | 11.1 | 91.8 | 0.12 | 0.15 |
| SEPARATOR 3 | 30 bar | 15° C. | FRACTION 3 | 1.5 | 83.8 | 0.04 | 0.07 |

Fatty Acids by Gas Chromatography.
Phytosterols (total of Campesterol, Stigmasterol and B-Silosterol) by Gas Chromatography.
Fatty Alcohols (total of Hexacosanol, Octacosanol and Triacontanol) by Gas Chromatography.

TABLE 2

SUPERCRITICAL EXTRACTION OF SAW PALMETTO OIL WITH FRACTIONATION INTO A HIGH-STEROL FRACTION

| VESSEL | PRESSURE | TEMP. | FRACTION | YIELD % | % FATTY ACIDS | % STEROLS | % FATTY ALCOHOLS |
|---|---|---|---|---|---|---|---|
| EXTRACTOR | 500 bar | 80° C. | WHOLE EXTRACT | 13.2 | 92.2 | 0.252 | N.A. |
| SEPARATOR 1 | 180 bar | 62° C. | FRACTION 1 | 5.6 | 93.4 | 0.196 | 0.22 |
| SEPARATOR 2 | 30 bar | 15° C. | FRACTION 2 | 7.6 | 91.4 | 0.294 | N.A. |

Fatty Acids by Gas Chromatography.
Phytosterols (total of Campesterol, Stigmasterol and B-Silosterol) by Gas Chromatography.
Fatty Alcohols (total of Hexacosanol, Octacosanol and Triacontanol) by Gas Chromatography.

TABLE 3

SUPERCRITICAL EXTRACTION OF SAW PALMETTO OIL WITH FRACTIONATION INTO A HIGH-STEROL FRACTION

| VESSEL | PRESSURE | TEMP. | FRACTION | YIELD % | % FATTY ACIDS | % STEROLS | % FATTY ALCOHOLS |
|---|---|---|---|---|---|---|---|
| EXTRACTOR | 500 bar | 80° C. | WHOLE EXTRACT | 14.1 | 90.6 | 0.24 | 0.25 |
| SEPARATOR 1 | 220 bar | 70° C. | FRACTION 1 | 1.6 | 85.9 | 0.57 | 0.57 |
| SEPARATOR 2 | 30 bar | 15° C. | FRACTION 2 | 12.5 | 92.2 | 0.19 | 0.25 |

Fatty Acids by Gas Chromatography.
Phytosterols (total of Campesterol, Stigmasterol and B-Silosterol) by Gas Chromatography.
Fatty Alcohols (total of Hexacosanol, Octacosanol and Triacontanol) by Gas Chromatography.

TABLE 4

SUPERCRITICAL EXTRACTION OF SAW PALMETTO OIL WITH FRACTIONATION INTO A HIGH-STEROL FRACTION

| VESSEL | PRESSURE | TEMP. | FRACTION | YIELD % | % FATTY ACIDS | % PHYTO-STEROLS | % FATTY ALCOHOLS | TOCO-PHEROLS | B-CAROTENE |
|---|---|---|---|---|---|---|---|---|---|
| EXTRACTOR | 500 bar | 80° C. | WHOLE EXTRACT | 13.8 | N.A. | N.A. | N.A. | N.A. | N.A. |
| SEPARATOR 1 | 260 bar | 75° C. | FRACTION 1 | 0.74 | 59.30 | 2.0 | 1.80 | 103 mg/100 g | 1.18 m IU/100 g |
| SEPARATOR 2 | 30 bar | 15° C. | FRACTION 2 | 13.06 | N.A. | N.A. | N.A. | N.A. | N.A. |

Fatty Acids by Gas Chromatography.
Phytosterols (total of Campesterol, Stigmasterot and B-Silosterol) by Gas Chromatography.
Fatty Alcohols (total of Hexacosanol, Octacosanol and Triacontanol) by Gas Chromatography.
Tocopherols (total alpha, delta, gamma) by High Performance Chromatography plus Tocotrienols by Gas Chromatography.
Beta Carotene by High Performance Gas Chromatography.

The free fatty acid composition of saw palmetto extract is rich in the shorter chain length fatty acids such as the capric, caprylic, lauric, and myristic acid. Palmitic, stearic, oleic, linoleic, and linolenic acid are also included with a number of ester form fatty acids in the ethyl-ester form. Different phytosterols include beta-sitosterol, stig masterol, cycloartenol, stigmas terol, cycloartenol, lupeol, lupenone, campesterol, and 24-methyl-cycloartenol. Other constituents include the aliphatic alcohols (C26-30), polyprenic compounds, flavonoids, glucose, galactose, arabinose, uronic acid, and other polysacharrides.

An analysis of the saw palmetto standardized extract that is at least 90% free fatty acids indicates it is yellow in color and soluble in hexane and the loss on drying, in one example, is about 5.5%. The largest proportion of fatty acids include oleic acid of about 40%, followed by lauric acid of about 20%, and myristic acid of about 12%, and palmitic acid of about 8%. This is followed in order by linoleic acid, stearic acid, linolenic acid, caprylic acid, and capric acid. In one example, the acid value is about 148.6 and saponification value about 222. This is only one non-limiting example.

Possibilities for the action of the saw palmetto extract include reducing the amount of dihydrotestosterone (DHT) and prostate tissue and inhibiting the binding of DHT to androgen receptors and prostate cells and establishing the anti-estrogenic action in the prostate tissue. Another possibility is the compounds in saw palmetto extract reduce the action of the insulin-like growth factor (IGF-1) action on prostate tissue. A typical common dosage is 320 milligrams of 80-90% liposterolic saw palmetto extract or even a 640 milligram of a 40-50% saw palmetto extract. It is possible to give multiple dosages of 180 milligrams of the higher percentage saw palmetto extract.

As noted before, the carotenoid is a tomato lycopene complex that among the carotenes is an efficient quencher of singlet oxygen free radicals and supports skin and prostate and cardiovascular health. The lycopene complex includes the natural tomato lycopene plus naturally occurring phytonutrients, including phytoene, phytofluene, tocopherols, and beta-carotene. It can be formed as beadlets with a concentration of 5% or 10% and used in tablets and capsules. It may be a micro-encapsulated powder (DC grade) and having a concentration of 6% or 10% and used in tablets. It may also be formed as an oleoresin (oil) having a concentration of 5%, 7%, 10%, 15%, and 18% and used in soft gels. It may also be formed as a cold water disbursable powder (CWD) having a concentration of 6% and 10% and used as a food fortification for cold water soluble (suspensions) having a concentration of 3% and 6% and used as a functional beverage.

The lycopene is a naturally lycopene as compared to a synthetic lycopene that contains only lycopene extract. As noted before, the lycopene can be formed for time release such as a multi-carotene beadlet formation. It is known that lycopene is not an essential nutrient for humans, but is commonly found in the diet from tomatoes and other dietary sources. It is absorbed in the intestine and transported in the blood by various lipoproteins and accumulates primarily in the blood, adipose tissue, skin, liver, adrenal glands, prostate and testes. Because it is absorbed in the intestine, it is not necessary or desirable based on the adverse reaction with saw palmetto extract to allow the lycopene to be delivered in the stomach and react with the saw palmetto extract.

In its natural, all-trans form, the lycopene molecule is long and straight and constrained by its system of 11 conjugated double bonds. Each extension in this conjugated system reduces the energy required for electrons to transition to higher energy states, allowing the molecule to absorb the visible light of aggressively longer wavelengths of visible light, so it appears red. When exposed to light or heat, the lycopene may undergo isomerization to different cis-isomers having a bent rather than linear shape. The high stability is 5-cis, which is greater than the all-trans, which is greater than 9-cis, which is greater than the 13-cis, which is greater than the 15-cis and the 7-cis, and the 11-cis as the lowest. The various cis-isomers constitute more than 60% of the total lycopene concentration in the bloodstream. Lycopene is insoluble in water and is dissolved in organic solvents and oils. Because of its non-polarity, it will stain sufficiently porous material including plastics.

Once ingested, it is believed that lycopene is incorporated into lipid micelles in the small intestine that are formed from dietary fats and bile acids and solubilize the hydrophobic lycopene and allow it to permeate the intestinal mucosal cells by a passive transport mechanism. Lycopene is incorporated into chylomicrons and released into the lymphatic system. Lycopene is also distributed in very low and low density lipoprotein fractions. It is possible that the lycopene used in combination with saw palmetto would decrease sun damage.

The combination of saw palmetto and lycopene may have synergistic effects when delivered together, the saw palmetto in the stomach and the lycopene in the duodenum. It may be used to treat acne and help hair loss and regrowth. It is possible to help women who are suffering from polycystic ovarian syndrome (PCOS) and increase the libido in sex and help any impotence issues. It may also be used as an expectorant to control irritation of mucous tissues. In combination with lycopene, it may reduce the incidence of cancer and increase antioxidant effects and reduce any asthma caused by exercise and reduce the chances of coronary artery disease (Arteriosclerosis). It may be used as a breast cancer preventative and cancer preventative in some cases. It may be used to aid eye disorders and used as a preventive therapy for age-related macular degeneration and cataracts. It may aid in treating gastrointestinal tract and colorectal cancer prevention and help gingivitis treatment and reduce high blood pressure. It may aid patients with oral mucusitis and preventive ovarian cancer treatment and prostate cancer preventative. It may aid in some protection and immune stimulation and lung function after exercise.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A dietary supplement delivery system for delivering a dietary supplement to humans to maintain prostate health, comprising:
    an outer capsule containing a supercritical $CO_2$ fluid derived saw palmetto extract containing at least 90 percent total saw palmetto lipids, wherein said lipids comprise fatty acids, sterols, and fatty alcohols; and
    an inner capsule within the outer capsule and containing lycopene, wherein the outer capsule is formed to dissolve in the stomach when ingested to release into the stomach supercritical $CO_2$ fluid derived saw palmetto extract and the inner capsule is formed to pass into the duodenum to dissolve and release the lycopene into the duodenum.

2. The delivery system according to claim 1, wherein the saw palmetto extract is made by a process comprising extracting the saw palmetto lipids by contacting ground saw palmetto berries with a substantially continuous flow of carbon dioxide under pressure.

3. The delivery system according to claim 1, wherein said lycopene comprises a tomato extract.

4. The delivery system according to claim 1, wherein said lycopene comprises a plurality of lycopene beadlets.

5. The delivery system according to claim 1, wherein said inner capsule comprises an acid resistant coating to prevent said inner capsule from dissolving within the stomach and allowing the inner capsule to pass into the duodenum and dissolve within the duodenum.

6. The delivery system according to claim 1, wherein said lycopene comprises an acid resistant timed released lycopene.

7. The delivery system according to claim 6, wherein said timed released lycopene comprises a beadlet formed to release the lycopene over a period of time within the duodenum.

8. A dietary supplement delivery system for delivering a dietary supplement to humans to maintain prostate health, comprising:
    an outer capsule containing a supercritical $CO_2$ fluid derived saw palmetto extract containing at least 90 percent total saw palmetto lipids, wherein said lipids comprise fatty acids, sterols, and fatty alcohols; and
    an inner capsule within the outer capsule and containing lycopene comprising a tomato extract, wherein the outer capsule is formed to dissolve in the stomach when ingested to release into the stomach the supercritical CO2 fluid derived saw palmetto extract and the inner capsule is formed to pass into the duodenum to dissolve and release the lycopene into the duodenum.

9. The delivery system according to claim 8, wherein the supercritical $CO_2$ fluid derived saw palmetto extract containing free fatty acids is made by a process comprising extracting the saw palmetto lipids by contacting ground saw palmetto berries with a substantially continuous flow of carbon dioxide under pressure.

10. The delivery system according to claim 8, wherein said lycopene comprises a plurality of lycopene beadlets.

11. The delivery system according to claim 8, wherein said inner capsule comprises an acid resistant coating to prevent said inner capsule from dissolving within the stomach and allowing the inner capsule to pass into the duodenum and dissolve within the duodenum.

12. The delivery system according to claim 8, wherein said lycopene comprises an acid resistant timed released lycopene.

13. The delivery system according to claim 12, wherein said timed released lycopene comprises a beadlet formed to release the lycopene over a period of time within the duodenum.

* * * * *